United States Patent [19]

Rogne et al.

[11] Patent Number: 4,801,020

[45] Date of Patent: Jan. 31, 1989

[54] APPARATUS AND METHOD FOR DETECTING DEFECTS IN A SPHERICAL OBJECT

[76] Inventors: Conrad O. Rogne, 2166 Yorktown; Charles H. Franklin, 1902 Longshore Dr.; Clarence S. Vinton, 1826 Traver St., all of Ann Arbor, Mich. 48105

[21] Appl. No.: 40,604

[22] Filed: Apr. 21, 1987

[51] Int. Cl.[4] ............... B07C 5/00; G01B 5/28
[52] U.S. Cl. ............... 209/538; 209/598; 73/105
[58] Field of Search ............... 209/538, 591, 598, 657; 73/105; 33/569

[56] References Cited

U.S. PATENT DOCUMENTS

| | | |
|---|---|---|
| 2,051,695 | 8/1936 | Glacy . |
| 2,701,055 | 2/1955 | Strom . |
| 2,778,497 | 1/1957 | Bickley . |
| 2,845,177 | 7/1958 | Perkins et al. . |
| 2,982,402 | 5/1961 | Dion . |
| 3,034,396 | 5/1962 | Wilcox . |
| 4,103,776 | 8/1978 | Tangiguchi ............... 209/591 |
| 4,551,677 | 11/1985 | Bankston ............... 324/226 |
| 4,580,097 | 4/1986 | Bartlett . |
| 4,644,274 | 2/1987 | Casarcia ............... 324/237 |

FOREIGN PATENT DOCUMENTS

| | | | |
|---|---|---|---|
| 693241 | 10/1979 | U.S.S.R. . | |
| 868546 | 9/1981 | U.S.S.R. . | |
| 911004 | 3/1959 | United Kingdom | 209/598 |
| 1171353 | 11/1969 | United Kingdom | 73/105 |

*Primary Examiner*—William L. Freeh
*Attorney, Agent, or Firm*—Ian C. McLeod

[57] ABSTRACT

An apparatus wherein a spherical object is rotated on its equatorial axis (b-b) and its polar axis (a-a) adjacent a sensor (s) for detecting defects is described. The roller shaft (128) has spherical projections (129 and 130) and spaced apart parallel spindles or shafts (127) with a ball support (131) which provides centering of the spherical object or ball (B) regardless of the diameter. Preferably multiple test cage assemblies (12) are used for balls of various sizes to insure stability of the ball during testing. The apparatus is particularly used for testing of ball-bearings for defects.

18 Claims, 4 Drawing Sheets

APPARATUS AND METHOD FOR DETECTING DEFECTS IN A SPHERICAL OBJECT

BACKGROUND OF THE INVENTION (1) Summary of the Invention

The present invention relates to a method and apparatus for detecting defects, surface or internal, in a spherical object. In particular the present invention relates to a method and apparatus wherein the spherical object is simultaneously rotated on its polar and equatorial axis adjacent a detector means which senses the defects. The ball is in contact with drive roller means which cause rotation in the vertical axis to thereby produce precise precession of the ball and scanning in one-half horizontal revolution of the ball.

(2) Prior Art

Various means have been used to detect defects in spherical objects, particularly ball bearings. U.S. Pat. No. 2,051,695 to Glacy (1936) describes a device for rotating spherical objects on a horizontal and vertical axis for testing. The problem is that the device is adapted to test only one size of spherical object. The testing of the ball is random in that the surface is not tested in a precise precession of the ball. Other less closely related patents describing the testing of spherical objects are U.S. Pat. Nos. 2,701,055 to Strom (1955); 2,778,497 to Bickley (1957); 2,845,177 to Perkins et al (1958); 2,982,402 to Dion (1961); 3,034,396 to Wilcox (1962) and 4,580,097 to Bartlett (1986). Soviet Union Patent Nos. 693241 (1979) and 868546 (1981) generally describe using eddy current testing of balls. U.S. Pat. No. 4,551,677 to Bankston (1985) also shows eddy current detectors.

GENERAL DESCRIPTION

The present invention relates to an apparatus for locating defects in spherical objects having varying diameters which comprises: shaft means rotatable on a vertical longitudinal axis and having an upper end and a lower end; housing means supporting the shaft means for rotation on the vertical longitudinal axis; drive means connected to the shaft means for rotating the shaft means; head means removably connected to the upper end of the shaft means and supported for rotation in a horizontal plane by the shaft means; drive roller means mounted on the head means and rotatable on a horizontal axis for rotating the spherical object resting on the roller means on the vertical longitudinal axis about a vertical plane as the head means and spherical object are rotated in the horizontal plane, wherein the spherical object is centered on the vertical axis of rotation by the drive roller means regardless of the diameter of the spherical object; and detection means mounted on the frame means adjacent the spherical object for locating the defects in the spherical object when rotated by the head means and drive roller means wherein there is a precise precession of the spherical object past the detection means.

Further the present invention relates to an apparatus for locating defects in spherical objects having varying diameters which comprises: a shaft rotatable on a vertical longitudinal of the apparatus and having an upper end and a lower end; a first housing surrounding and supporting the shaft for rotation on the vertical longitudinal axis; a second housing supporting the first housing around the vertical longitudinal axis; a motor with a drive pulley mounted in the second housing; a driven pulley mounted for rotation in the second housing around the vertical longitudinal axis; coupling means connecting the driven pulley and shaft for rotation of the shaft in the first housing; an endless belt connecting the pulleys; a drive head removably mounted on the first housing and coupled to the shaft for rotation in a horizontal plane around the vertical longitudinal axis by the motor, pulleys and belt; a pair of spaced apart drive rollers mounted in the head and rotatable on a horizontal axis for rotating the spherical object resting on the rollers on the longitudinal axis about a vertical plane as the head means spherical object are rotated in the horizontal plane, wherein the spherical object is centered on the vertical axis of rotation by the drive rollers regardless of the diameter of the spherical object; and detection means mounted on the first housing adjacent the spherical object for locating the defects in the spherical object as it is rotated by the head and drive rollers, wherein there is a precise precession of the spherical object past the detection means.

Finally the present invention relates to a method for determining defects in spherical objects having varying diameters which comprises: providing an apparatus for locating defects in spherical objects which comprises shaft means rotatable on a vertical longitudinal axis and having an upper end and a lower end; housing means supporting the shaft means for rotation on the vertical longitudinal axis; drive means connected to the shaft means for rotating the shaft means; head means removably connected to the upper end of the shaft means and supported for rotation in a horizontal plane by the shaft means; drive roller means mounted on the head means and rotatable on a horizontal axis for rotating the spherical object resting on the roller means on the vertical longitudinal axis about a vertical plane as the head means and spherical object are rotated in the horizontal plane, wherein the spherical object is centered on the vertical axis of rotation by the drive roller means regardless of the diameter of the spherical object; and detection means mounted on the frame means adjacent the spherical object for locating the defects in the spherical object when rotated by the head means and drive roller means; and segregating multiple of the spherical objects depending upon whether or not they have the defects using the detection means, wherein there is precise precession of the spherical object past the detection means.

The drive roller means preferably comprises two (2) parallel shafts that have spherical surfaces which contact the spherical object such that the spherical object is centered on the roller means regardless of the diameter of the spherical object. The shafts can each have two spherical surfaces and be equidistant from the center of rotation or one shaft can have two (2) spherical surfaces and the other shaft is merely a driving surface. The centers of the surfaces must be equidistant from the vertical axis of rotation and preferably on 120° centers. This system provides the precise precession or movement of the ball for scanning by the detection means.

The detection means can by optical, such as a laser or other light source for detecting surface defects and electromagnetic such as an eddy current source or ultrasonic source for detecting external or internal defects on or in the spherical object. Numerous variations of the detection means will occur to those skilled in the art.

SPECIFIC DESCRIPTION

Figure 1:
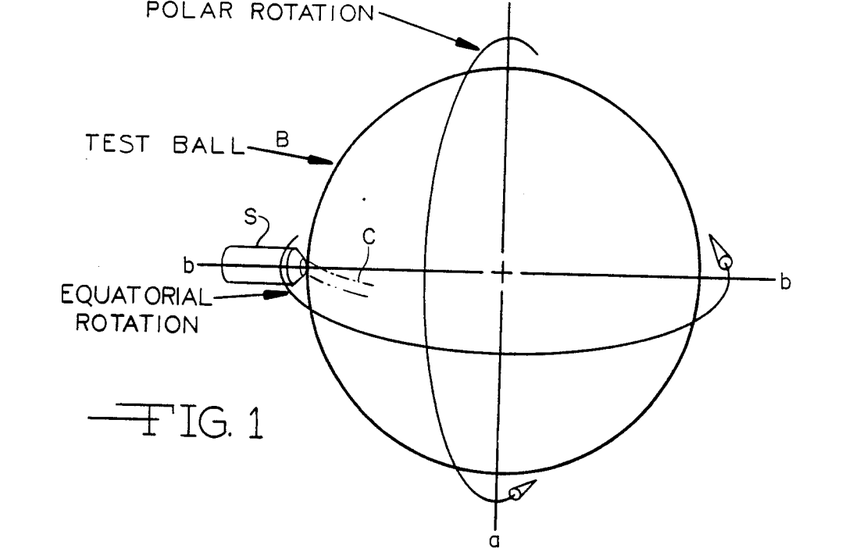
FIG. 1 is a front perspective view of a spherical object B showing the simultaneous rotation of the object on the polar axis a-a and the equatorial axis b-b which allows detection of defects by sensor S.

FIG. 1 shows a sphere or ball B, such as a ballbearing, which is simultaneously rotated on its polar axis a-a and its equatorial axis b-b as shown by the arrows. A sensor S on the equatorial axis b-b scans a band or region c of the sphere B adjacent the sensor S.

Figure 2:
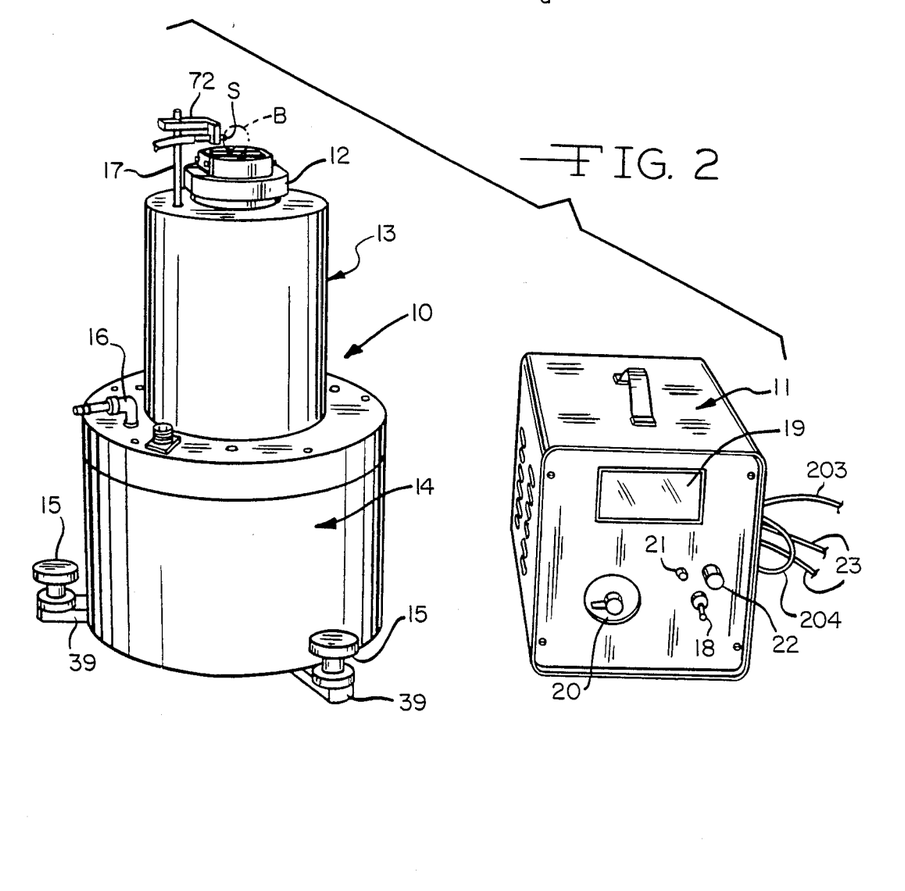
FIG. 2 is a front perspective view of the apparatus of the present invention showing the apparatus 10 and a console 11 for controlling the apparatus.

FIG. 2 shows the preferred test machine or assembly 10 for rotating the sphere B in the manner shown in FIG. 1 and a control console 11.

The machine or assembly 10 includes a removable ball test cage assembly 12, an upper housing 13 supporting the assembly 12 and a lower housing 14 supporting the upper housing 13. Three (3) leveling screws 15 (two shown) are provided on the bottom of the lower housing 14. An air inlet port 16 is provided on the lower housing 14. A post 17 is provided for supporting the sensor S adjacent the sphere B.

The console 11 includes an off-on switch 18, a digital tachometer dial 19, a motor speed varying switch 20, off-on light 21, fuse 22 and cables 23 mounted to a power source and to the test assembly 10.

Figure 3:
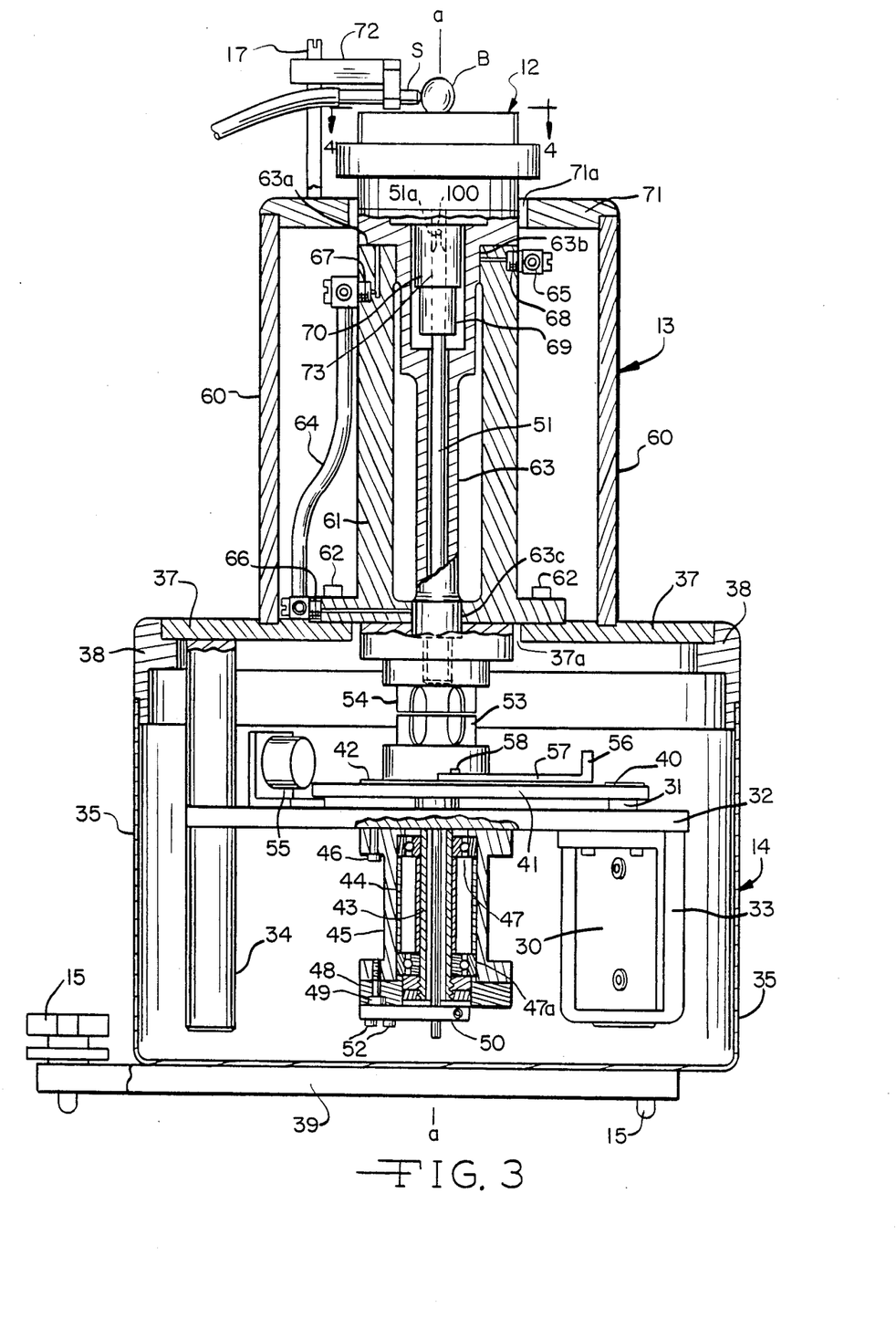
FIG. 3 is a front cross-sectional view of the apparatus 10 shown in FIG. 2, particularly showing an upper housing 13 supporting a lower housing 14 with a rotatable shaft 63 in the upper housing driven by a pulley 42 in the lower housing.

FIG. 3 shows the details inside the upper and lower housings 13 and 14. The lower housing 14 includes a motor 30 with a vertically oriented shaft 31 projecting through a horizontal secondary mounting plate 32. The motor 30 is housed in a frame 33. The secondary mounting plate 32 is supported in the lower housing 14 by a support 34 adjacent to cup shaped member 35 forming the lower housing 14. The plate 32 is also supported by a spacer 36 projecting downward from a cover 37 from the lower housing 14. A ring 38 joins the member 35 and cover 37. The member 35 is supported on leveling plate 39 which supports screws 15 for leveling of the plate 39 and thus the assembly 10.

The shaft 31 of motor 30 supports a pulley 40 which in turn supports a belt 41 around a large pulley 42 mounted on a large shaft 43 which is on the polar axis of rotation a-a of the sphere B. The shaft 43 is supported on plate 32 and extends vertically downward into a lower bearing assembly 44 along axis a-a. The assembly 44 includes a cage 45 secured by bolt 46 to the plate 32, vertically spaced apart ball bearings 47 and 47a and a lower holder 48 secured to cage 45 by bolts 49. A clamp 50 is mounted on the holder 48 and extends over axis a-a to clamp a rod 51 which extends upward through the lower housing 14 and through the upper housing 13 to adjacent the cage assembly 12. The clamp 50 is secured to the holder 48 by bolts 52.

The large pulley 42 supports a lower magnet drive coupling 53 which is in closely spaced relationship to an upper magnetic drive coupling 54. The magnetic field between the couplings 53 and 54 drives the upper coupling 54 when the motor 30 is turned on. This type of indirect coupling reduces vibration in the assembly 10. A tachometer 55 is supported on plate 32 and detects the passage of a flag 56 on an arm 57 secured by bolt 58 to the pulley 42.

Thus as can be seen from FIG. 3 the motor 30 which is activated by switch 18 on console 11 rotates in turn pulley 40, belt 41, large pulley 42 and lower coupling 53 to thus rotate the upper coupling 54. The clamp 50 holds the rod 51. A transmission or motor (not shown) can be used to vary the degree of precession per revolution of the ball B. The tachometer 55 allows measurement of the rotation rate of the pulley 42. Screws 15 assure that the assembly 10 is level which is important for operation.

The upper assembly 13 includes cylindrical member 60 mounted on cover 37 around axis a-a. The upper coupling 54 projects downward from the lower end of the assembly 13 into an opening 37a in cover 37 and is held in place by a main bearing housing 61 bolted to cover 37 by bolts 62. A main shaft 63 extends upward from upper coupling 54 vertically around axis a-a and is supported by housing 61. Air conduit 64 and 65 lead to ports 66, 67 and 68 leading through the housing 61 to supply air to the bearing spots 63a, 63b and 63c on shaft 66. The conduits 64 and 65 are supplied air by air inlet port 16 (FIG. 1). The shaft 63 is hollow and rod 51 extends through the shaft 63 to a transmission reduction drive 69 (preferably 30:1) on axis a-a connected to an adaptor 70 leading to cage assembly 12.

As can be seen shaft 63 rotates independently of rod 51 and provides equatorial rotation on axis b-b for the ball or sphere B on assembly 12. The cylindrical member 60 includes a cover 71 with an opening 71a through which an enlarged portion 63b of shaft 63 extends. A main shaft adaptor 73 engages the ball cage assembly 12 along the axis a-a. FIG. 3 also shows a clamp 72 for sensor S mounted on post 17 which is secured to the cover 71. The clamp 72 holds the sensor S and generally is adapted to swing the sensor S into and out of position adjacent the ball B.

FIG. 4 to 7 shows the details of the ball cage assembly 12 for accomplishing rotation of the sphere B on polar axis a-a and equatorial axis b-b. Along the axis a-a, a drive rod 100 with a slot 100a engages the rod 73. The rod 100 is part of a miter gear box assembly 101 shown in detail in FIG. 7. The assembly 101 includes a shaft 103 vertically mounted on axis a-a on spaced apart bearings 104 and 105 and threaded into a holder 106 on adaptor 107. Gear 108 rotates on the axis a-a. Matching right angle gear 109 is mounted on shaft 110 and journaled on spaced apart bearings 111 and 112 in holder 106 with adaptor 113 holding bearing 111 on shaft 110 in place. The shaft 110 as also journaled on bearings 114 and 115 secured in housing 116 by adaptors 117 and 118. Set screws 119 and 120 urge ball bearings 121 and 122 against opposite ends of shaft 110. The set screws 119 and 120 and ball bearings 121 and 122 provide a means for adjusting for end play.

Figures 4, 5, 6:
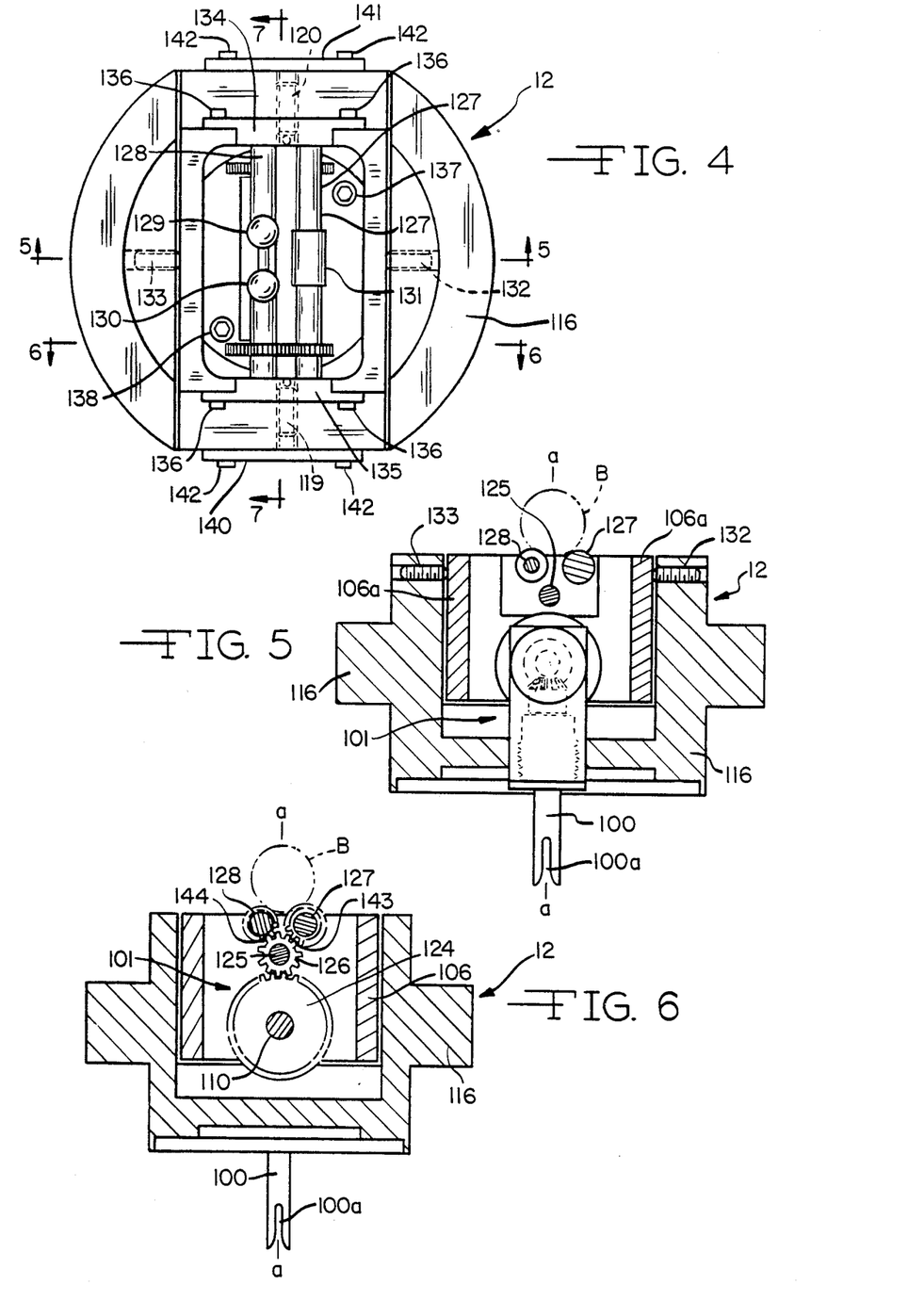
FIG. 4 is a plan view of a removable cage assembly 12 supporting the sphere B rotation on the polar axis a-a and the equatorial axis b-b.
FIG. 5 is a front cross-sectional view along line 5—5 of FIG. 4, particularly showing a cage unit 106 supporting shafts 127 and 128 which support the ball B for rotation on polar axis a-a.
FIG. 6 is a front cross-sectional view along line 6—6 of FIG. 4 particularly showing gears 124, 126, 143 and 144 for rotating the shafts 127 and 128.
Figure 7:
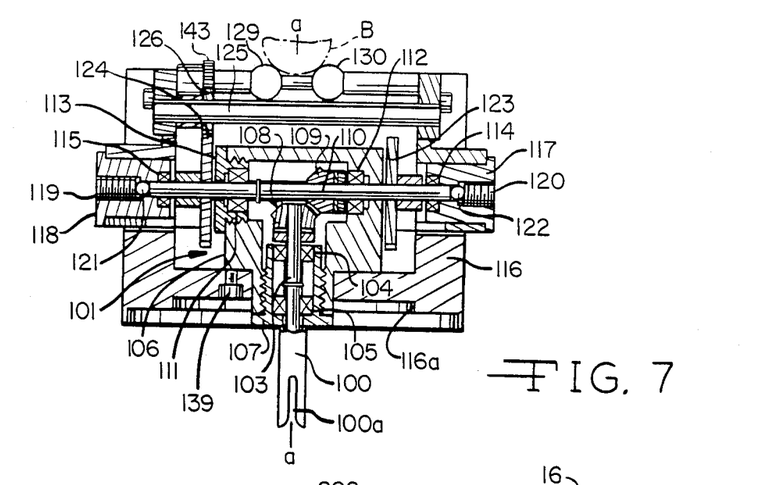
FIG. 7 is a front cross-sectional view along line 7—7 of FIG. 4 particularly showing the shafts 110, 125, 127 and 128 for rotating the sphere B.

Secured to shaft 110 is a spacer 123 which acts to balance a large gear 124 secured to the opposite side of shaft 110 from axis a-a. An idler shaft 125 is mounted in housing 116 parallel to shaft 110 and supports an idler gear 126 engaging large gear 124. Two ball support spindles 127 and 128 are provided parallel to the idler shaft 125 and shaft 110 and to each other which support the ball B turned by gears 143 and 144. The shaft 128 has two spaced apart spherical projections 129 and 130 and spindle or shaft 127 has roller ball support 131 which engage the ball B to hold the ball B in position for rotation about the axis a-a and b-b. Set screws 132 and 133 (FIG. 5) in housing 116 allow for minor adjustment of the rotational positions of holder 106a in the housing 116. Plates 134 and 135 hold shaft 125 and spindles 127 and 128 in place in housing 106a by means of screws 136. Screws 137 and 138 hold the inner housing 116 onto the shaft 63. Plates 140 and 141 are held in place by screws 142 and secure shaft 110 in position on housing 116.

Thus as can be seen, the assembly 12 rotates the ball B on the polar axis a-a and equatorial axis b-b simultaneously. The housing 116 of assembly 12 is rotated vertically around axis a-a by shaft 63. At the same time the roller support 131 and spherical projections 129 and 130 rotate the ball B on axis b-b. As a result, a region C on the ball B is traced until the surface of the ball B is completely scanned, a result which takes very little time.

Figure 8:
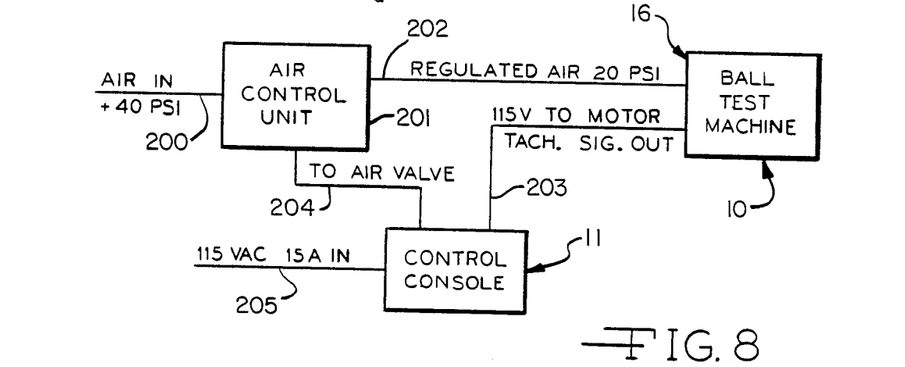
FIG. 8 is a schematic view of the air and electrical connections to the apparatus 10 from console 11.

FIG. 8 shows the air inlet through inlet 200 to an air control unit 201 which controls the air pressure to the test machine 10 through line 202 to inlet 16. The tachometer 55 signal is fed to the control console 11 by electrical cable 203 where it is directly read from on tachometer dial 19. A valve 206 (FIG. 9) in the unit 201 is electrically controlled by line 204 from console 11. Preferably a 115VAC electrical supply 205 is used.

Figure 9:
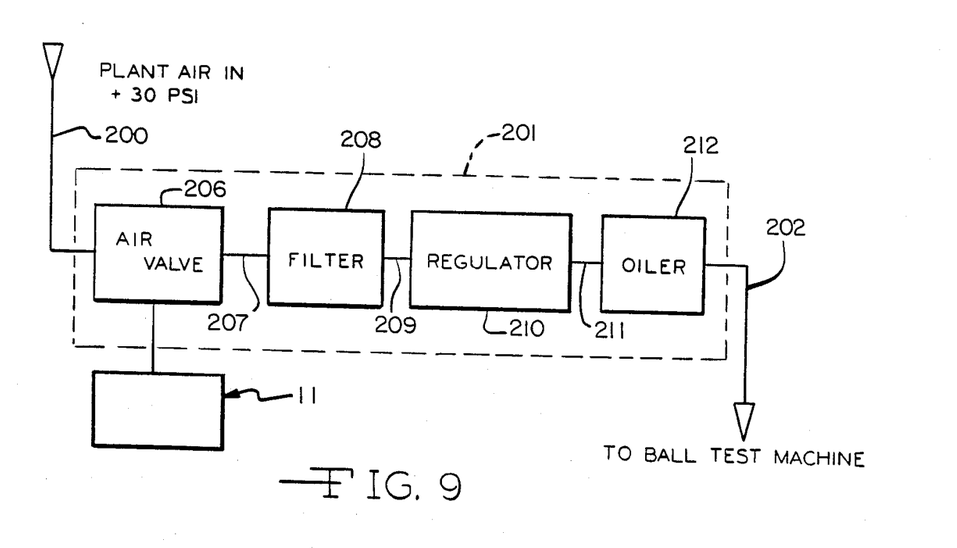
FIG. 9 is a schematic view of the air control unit 201 for conditioning the air to be supplied to air bearings 63a, 63b and 63c in apparatus 10.

FIG. 9 shows the details of the air supply including air valve 206 in the unit 201. The air flows through line 207 to filter 208 through line 209, regulator 210, line 211, oiler 212 and then through line 202 to machine 10. The machine 10 generally uses oil in the air supplied to the bearings to prevent wear.

It will be appreciated that the rod 51 can be rotated clockwise or counter-clockwise to alter the polar velocity along axis b-b of the sphere B with respect to the equatorial velocity of the sphere B along axis a-a. Also, it will be appreciated that the transmission 69 could be mounted at the lower end of the rod 51.

Ball Inspection Machine-General

The following is a description of the preferred operation of the apparatus of the present invention.

For best results, the test probes should be in very close proximity to the test ball B (0.005 inch or less) if the probes uses eddy current. The main shaft 63 transfers the rotational energy from the drive section to the cage assembly 12. The main shaft 63 is supported at sections 63a, 63b and 63c by air. The transmission 69 used to introduce incremental polar rotation on axis b-b proportional to the equatorial rotation on axis a-a. The equatorial rotation on axis a-a is optimized at a surface velocity of seven (7) inches (17.78 cm) per second. The polar rotation is optimized at increments of 0.023 inches per equatorial revolution. In order to properly energize the transmission 69, clamp 50 locks the transmission input rod 51, thus keying the polar rotation on axis b-b to the equatorial rotation on axis a-a. The equatorial rotation on axis a-a is monitored by the tachometer sensor 55 which sends its signals to the digital readout 19 on the control console. The lower housing 35 encloses and thus protects the system during operation. The machine 10 is controlled through the console 11. The spindle speed is controlled by the power control 20 on the control console 11. Shaft 63 speed is monitored by electronic tachometer 55 with digital readout 19 on the console 11. The main on-off switch 18 is interlocked with the air flow to the air bearings 63a, 63b and 63c. When switch 18 is initiated, the power light 21 illuminates. The entire internal circuit is protected by 3 AMP panel fuse 22.

On system start-up, the shaft 63 speed control 20 is set to zero. Air in excess of 20 psi should be present at the air control valve 206. When switching the system on, operational air and electricity is present as needed. The speed control 20 can be rotated to the desired shaft 63 speed. On first start-up, the system should be left running (350-500 rpm) to stabilize for approximately 15 minutes. If this is not done, the system will gradually increase shaft 63 speed until an operational temperature are reached. If the system is shut down frequently, such as while changing test balls B, the air supply should be continuous to the main bearings. This can accomplished by unplugging the air valve 206 power line 204 from in back of the console 11 (not shown) and plugging it directly into a 115V AC line. This will hold the air valve 206 open and operational speed will be achieved faster. During the time the air valve 206 is constantly open, the machine should be in steady use. To leave the power to the air valve 206 for long periods will not damage the unit but will consume excessive amounts of air. Clean air at 40 psi min. is supplied to the control unit air valve 206.

Other than the 115 VAC into the console 11, the cable 203 used to energize the air control valve and the machine 10 which contains the 115 VAC to the motor 30 and the tachometer signal return for processing and read-out at the console 11.

The equatorial velocity on axis a-a is the selected shaft 63 velocity for the test ball B diameter. The polar scan on axis b-b proceeds at a slower pace allowing for a 0.023 inch movement in circumference for each equatorial revolution on axis b-b. This relationship is fixed and holds true for any size ball B tested. Cage assemblies 12 were designed for a specific range of ball sizes as shown in Table 1. The variable is the operational test time. Table 2 provides the shaft 63 speed and test time for each ball B diameter.

TABLE 1

| Ball Test Cage Assembly 12 and Ball Size Range | |
|---|---|
| Ball Test Cage Number | Ball B Size Range |
| 1. | .250 Dia. to .375 Dia. |
| 2. | .375 Dia. to .500 Dia. |
| 3. | .500 Dia. to .813 Dia. |

TABLE 1-continued

| Ball Test Cage Assembly 12 and Ball Size Range | |
|---|---|
| Ball Test Cage Number | Ball B Size Range |
| 4. | .813 Dia. to 1.13 Dia. |

The ball B size range for each test cage was chosen in terms of the small diameter ball height/test probe relationship to the estimated maximum size for stability during rotation. The small size of each range must be considered absolute as only minimum probe S clearance is provided. It is possible to go over the maximum limit; however, positional instability of the ball B increases with increased ball size. A secondary consideration in ball size selection per cage assembly 12 was of ball B removal and placement in the automatic mode without stopping shaft 63 rotation.

TABLE 2

| Ball Rotation Velocity and Test Time Chart | | |
|---|---|---|
| Ball Diameter | RPM | Scan Time at Seven "/sec |
| 1/4 .250 inch | 534.759 | 1.916 sec. |
| 5/16 .3125 inch | 427.8 | 2.99 sec. |
| 11/32 .34375 inch | 388.925 | 3.622 sec. |
| 3/8 .375 inch | 356.506 | 4.31 sec. |
| 7/16 .4375 inch | 305.566 | 5.867 sec. |
| 1/2 .500 inch | 267.38 | 7.663 sec. |
| 9/16 .5625 inch | 237.664 | 9.698 sec. |
| 5/8 .625 inch | 216.886 | 11.645 sec. |
| 11/16 .6875 inch | 194.453 | 14.49 sec. |
| 3/4 .750 inch | 178.253 | 17.24 sec. |
| 13/16 .8125 inch | 164.538 | 20.24 sec. |
| 7/8 .875 inch | 152.788 | 23.472 sec. |
| 15/16 .9375 inch | 142.6 | 27.05 sec. |
| 1.0 inch | 133.69 | 30.653 sec. |
| 1.125 inch | 118.836 | 38.785 sec. |
| 1.250 inch | 106.952 | 47.88 sec. |
| 1.375 inch | 97.229 | 57.312 sec. |
| 1.500 inch | 89.127 | 68.98 sec. |

Air Valve/Regulator/Oiler Unit

The air supply is connected to the inlet side of the air control unit 201. The first stage is the air on/off valve 206. The second stage is a filter 208 and moisture trap. This must be checked every day. If any moisture is present, it must be washed and fully dried. If moisture is allowed to accumulate, excessive amounts will find its way to the main air bearings 63a, 63b and 63c. The third stage is the pressure regulator 210 which is set at 20 PSI. The last stage is the oiler 212 unit and it must maintain lubrication levels. During prolonged operation, the bearings 63a, 63b and 63c prefer a very small amount of lubricant. The lubricant is preferably a mixture of 5 parts kerosene to one part of light non-detergent machine oil. Proper lubricant rate is one oiler container full every 200 machine run hours.

Test Ball Alignment

FIGS. 5 to 7 show the cage assembly 12 with set screws 119 and 120 and 132 and 133 for each plane to center the ball B on axis a-a. To alter the adjustment, by using an Allen wrench, first remove the first set screws 132 and 133 which are for locking. This is done on both sides of the assembly 12 for each plane of adjustment. A 3/16 (0.1875) dia. drill gage rod (not shown), is placed into the probe holder 72 and pushed into the immediate proximity of the ball B. The height of the probe holder 72 on pole 17 is adjusted until the rod is centered on the ball B. The gaging rod is well centered on the ball B, the cage assembly 12 is rotated on axis a-a and visually observed for the change in the gap between the ball B and rod. The plane of greatest gap is noted and adjusted to reduce the gap by one-half (½). This process is continued until the gap remains constant with the test rod very close to the ball (0.0005). When this gap is constant through 360 degrees of rotation, the machine 10 is turned on and the constant setting is observed to see if it remains during continuous rotation. If not, the described positioning operation is repeated. When the rotational accuracy has been satisfied, set screws 119 and 120 are checked to be sure they are just applying pressure. All locking set screws are then replaced. When the system is tightened, one more centering test of the test ball B is performed to be sure there was no change in adjustment.

Removing and Installing the Ball Test Cage Assembly

The cage assembly 12 is constructed for optimized holding of a specific range of ball B sizes as set forth in Tables 1 and 2. Each test cage assembly 12 is pre-set to center the ball B on the center of rotation which does not change when the cage assembly 12 is removed. To remove the cage assembly from the upper housing 13, the two screws 137 and 138 are removed and the cage assembly 12 is lifted up and off the main shaft 63. When the top of the main shaft 63 is examined, the 2.875 Dia positioning boss on shaft 63 is exposed and a hole extending into the shaft 63 on axis a-a is seen. A cross pin 51a is provided on shaft 73. The shaft 73 extends up from a small reduction transmission used to control the polar rotation drive for the test ball B. The cross pin 51a is the drive key to engage shaft 100. Shaft 100 is slotted on the cage to engage the cross pin 51a.

Installation of the Test Ball Cage Assembly 12 is by lowering the assembly onto the drive shaft 63. When the cage assembly 12 seems seated, it is rotated gently until it drops into final position by engaging the shaft 51. The cage assembly 12 is then rotated and rotation of the shafts 127 and 128 is observed. Shafts 127 and 128 should rotate about their own axis while the ball cage assembly 12 is rotated. When the shaft 73 engagement has been verified, rotation of the cage assembly 12 is continued until the holes for the two screws 137 and 138 are aligned. The two screws 137 and 138 are aligned and tighten.

As can be seen the operation of the replacement of the cage assemblies for different ball B sizes is easily accomplished. Variations in the cage assembly 12 will occur to those skilled in the art. It is intended that the foregoing description be limited only by the hereinafter appended claims.

We claim:
1. An apparatus for locating defects in spherical objects having varying diameters which comprises:
   (a) shaft means rotatable on a vertical and longitudinal axis and having an upper end and a lower end;
   (b) housing means supporting the shaft means for rotation on the vertical and longitudinal axis;
   (c) drive means connected to the shaft means for rotating the shaft means;
   (d) head means connected to the upper end of the shaft means and supported for rotation in a horizontal plane by the shaft means;
   (e) drive roller means mounted on the head means and rotatable on a horizontal axis for rotating the spherical object resting on the roller means on the vertical and longitudinal axis about a vertical plane as the head means and spherical object are rotated in the horizontal plane, wherein the spherical object is centered on the vertical axis of rotation by the drive roller means regardless of the diameter of the spherical object; and (f) detection means mounted on the frame means adjacent the spherical object for locating the defects in the spherical object when rotated by the head means and drive roller means, wherein there is a precise precession of the spherical object past the detection means.

2. The apparatus of claim 1 wherein the rotatable shaft means is hollow along the vertical and longitudinal axis, wherein a rod means is mounted inside the hollow of the shaft along the vertical and longitudinal axis, wherein the rod means is connected to transmission means which in turn is connected to drive roller means by gear means connected to a second shaft mounted along the vertical and longitudinal axis on the head means and connected to the transmission means to thereby rotate the drive roller means upon rotation of the head means.

3. The apparatus of claim 1 wherein the detection means is an eddy current detection means which locate the defects in the spherical object.

4. The apparatus of claim 1 wherein the shaft means is driven at the lower end of the shaft means by an isolation coupling from the drive means.

5. The apparatus of claim 1 wherein the detection means includes means for swinging the detection means horizontally or vertically away from the spherical object to allow for loading and unloading of the spherical objects without damaging the detection means.

6. An apparatus for locating defects in spherical objects having varying diameters which comprises:
(a) a shaft rotatable on a vertical and longitudinal of the apparatus and having an upper end and a lower end;
(b) a first housing surrounding and supporting the shaft for rotation on the vertical and longitudinal axis;
(c) a second housing supporting the first housing at the lower end of the shaft around the vertical and longitudinal axis;
(d) a motor with a drive pulley mounted in the second housing;
(e) a driven pulley mounted for rotation in the second housing around the vertical and longitudinal axis;
(f) coupling means connecting the driven pulley and shaft for rotation of the shaft in the first housing;
(g) an endless belt connecting the pulleys;
(h) a drive head removably mounted on the first housing at the upper end of the shaft and coupled to the shaft for rotation in a horizontal plane around the vertical and longitudinal axis by the motor, pulleys and belt;
(i) a pair of spaced apart drive rollers mounted in the head and rotatable on a horizontal axis for rotating the spherical object resting on the rollers on the vertical and longitudinal axis about a vertical plane as the head means and spherical object are rotated in the horizontal plane, wherein the spherical object is centered on the vertical and longitudinal axis of rotation by the drive rollers regardless of the diameter of the spherical object; and
(j) detection means mounted on the first housing adjacent the spherical object for locating the defects in the spherical object as it is rotated by the head and drive rollers, wherein there is a precise precession of the spherical object past the detection means.

7. The apparatus of claim 6 wherein the coupling means is a pair of spaced apart magnets one mounted on the driven pulley and the other mounted on the lower end of the shaft.

8. The apparatus of claim 6 wherein the shaft is hollow along the vertical and longitudinal axis, wherein a rod is mounted inside the hollow of the shaft along the vertical and longitudinal axis, wherein the rod is connected to transmission means which in turn is connected to the drive rollers by gear means connected to a second shaft mounted along the vertical and longitudinal axis on the head means and connected to the transmission means to thereby rotate the drive rollers.

9. The apparatus of claim 6 wherein the detection means is an eddy current detection means.

10. The apparatus of claim 6 wherein the shaft is mounted on air bearings in the first housing.

11. The apparatus of claim 6 wherein a tachometer means is provided in the first or second housing to measure the rotation of the shaft.

12. The apparatus of claim 6 wherein the shaft is hollow along the vertical and longitudinal axis, wherein a rod is mounted inside the hollow of the shaft along the vertical and longitudinal axis, wherein the rod is connected to a transmission means which in turn is connected to the drive rollers as in claim 8 to thereby rotate the drive rollers;
wherein the detection means provides a magnetic eddy current to the spherical object which comprises a to locate defects;
wherein the shaft is mounted on air bearings in the first housing; and
wherein a tachometer means is provided in the first or second housing to measure the rotation of the shaft.

13. A method for determining defects in spherical objects having varying diameters which comprises:
(a) providing an apparatus for locating defects in spherical objects which comprises shaft means rotatable on a vertical and longitudinal axis and having an upper end and a lower end; housing means supporting the shaft means for rotation on the vertical and longitudinal axis; drive means connected to the shaft means for rotating the shaft means; head means removably connected to the upper end of the shaft means and supported for rotation in a horizontal plane by the shaft means; drive roller means mounted on the head means and rotatable on a horizontal axis for rotating the spherical object resting on the roller means on the vertical and longitudinal axis about a vertical plane as the head means and spherical object are rotated in the horizontal plane, wherein the spherical object is centered on the vertical axis of rotation by the drive roller means regardless of the diameter of the spherical object; and detection means mounted on the frame means adjacent the spherical object for locating the defects in the spherical object when rotated by the head means and drive roller means; and
(b) separating multiple of the spherical objects depending upon whether or not they have the defects using the detection means, wherein there is precise precession of the spherical object past the detection means.

14. The method of claim 13 wherein a holder for the detection means is moved away from the vertical and longitudinal axis while placing a spherical object to be on the apparatus.

15. The method of claim 13 wherein the detection means is an eddy current detection means and wherein the spherical objects are segregated by means of the eddy current.

16. The method of claim 14 wherein the defects which are detected are internal and sufficient to cause the spherical object to break apart under a load in use.

17. An apparatus for locating defects in spherical objects having varying diameters which comprises:
(a) shaft means rotatable on a vertical and longitudinal axis and having an upper end and a lower end;
(b) housing means supporting the shaft means for rotation on the vertical and longitudinal axis;
(c) drive means connected to the shaft means for rotating the shaft means;
(d) head means connected to the upper end of the shaft means and supported for rotation in a horizontal plane by the shaft means;
(e) two parallel spaced apart drive roller means mounted on the head means and rotatable on a horizontal axis for rotating the spherical object resting on the roller means on the vertical and longitudinal axis about a vertical plane as the head means and spherical object are rotated in the horizontal plane, wherein the drive roller means includes two spaced apart spherical contact surfaces mounted on one of the drive roller means and a circularly cross-sectioned drive surface on the other of the drive roller means wherein the spherical contact surfaces and the drive surface have equal diameters in contact with the spherical object such that the spherical object is centered on the vertical and longitudinal axis of rotation by the drive roller means regardless of the diameter of the spherical object; and
(f) detection means mounted on the frame means adjacent the spherical object for locating the defects in the spherical object when rotated by the head means in drive roller means wherein there is a precise precession of the spherical object past the detection means.

18. The apparatus of claim 17 wherein the rotatable shaft means is hollow along the vertical and longitudinal axis, wherein a rod means is mounted inside the hollow of the shaft along the vertical and longitudinal axis, wherein the rod means is connected to transmission means which in turn is connected to the drive roller means by gear means as in claim 8 to thereby rotate the drive roller means upon rotation of the head means.

* * * * *

UNITED STATES PATENT AND TRADEMARK OFFICE
CERTIFICATE OF CORRECTION

PATENT NO.   : 4,801,020

DATED        : January 31, 1989

INVENTOR(S)  : Conrad O. Rogne, Charles H. Franklin and Clarence S. Vinton

It is certified that error appears in the above—identified patent and that said Letters Patent is hereby corrected as shown below:

Column 5, line 64, "0.005" should be --0.0005--.

Column 5, line 65 "uses" should be --use--.

Column 6, line and 33 "are" should be --is--.

Column 6, line 35, --be-- should be inserted before "accomplished".

Column 9, line 17 (Claim 2) insert --the-- after "to".

Column 10, lines 33 and 34 (Claim 12) delete "which comprises a".

Signed and Sealed this

First Day of August, 1989

Attest:

DONALD J. QUIGG

Attesting Officer

Commissioner of Patents and Trademarks